United States Patent
Wolleschensky (10) Patent No.: US 8,699,130 B2
(45) Date of Patent: Apr. 15, 2014

(54) MICROSCOPE, IN PARTICULAR LASER SCANNING MICROSCOPE

(75) Inventor: Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 84 days.

(21) Appl. No.: 13/255,627

(22) PCT Filed: Mar. 6, 2010

(86) PCT No.: PCT/EP2010/001417
§ 371 (c)(1),
(2), (4) Date: Sep. 9, 2011

(87) PCT Pub. No.: WO2010/102767
PCT Pub. Date: Sep. 16, 2010

(65) Prior Publication Data
US 2011/0317258 A1    Dec. 29, 2011

(30) Foreign Application Priority Data

Mar. 12, 2009 (DE) .......................... 10 2009 012 874

(51) Int. Cl.
*G02B 21/36*  (2006.01)
*G02B 21/00*  (2006.01)

(52) U.S. Cl.
CPC ........ *G02B 21/0076* (2013.01); *G02B 21/0064* (2013.01)
USPC .......................................... 359/368; 359/363

(58) Field of Classification Search
USPC .................. 359/368–398, 722–723
See application file for complete search history.

(56) References Cited

U.S. PATENT DOCUMENTS

| | | | |
|---|---|---|---|
| 6,309,078 B1 | 10/2001 | Dromaretsky et al. | |
| 6,525,875 B1 * | 2/2003 | Lauer | 359/368 |
| 6,909,549 B1 * | 6/2005 | Hsieh et al. | 359/578 |
| 7,410,793 B2 * | 8/2008 | Boege et al. | 356/73 |
| 7,554,664 B2 * | 6/2009 | Wolleschensky et al. | 359/618 |
| 2002/0176162 A1 | 11/2002 | Borlinghaus | |

FOREIGN PATENT DOCUMENTS

| | | |
|---|---|---|
| DE | 198 35 068 | 2/2000 |
| DE | 10 2004 029733 | 2/2005 |
| DE | 19835070 | 3/2006 |
| DE | 10 2006 03490 | 1/2008 |
| EP | 1 882 969 | 1/2008 |

OTHER PUBLICATIONS

Machine Translation (German to English) of DE 19835068 by Wolleschensky.*

(Continued)

*Primary Examiner* — Stephone B Allen
*Assistant Examiner* — Jeffrey Madonna
(74) *Attorney, Agent, or Firm* — Frommer Lawrence & Haugh LLP (57) ABSTRACT

Microscope, particularly laser scanning microscope, for optical detection of light radiation excited in a specimen, having a detection beam path for detecting spectral components of the light radiation in a plurality of detection channels, wherein the light radiation arrives at a variable longpass filter or shortpass filter from which reflected and/or transmitted components are reflected back with a parallel offset, and the latter arrive at a detector after at least one back-reflection of this kind.

13 Claims, 6 Drawing Sheets

(56) References Cited

OTHER PUBLICATIONS

Notification of Translation of the International Preliminary Report on Patentability dated Sep. 29, 2011, International Bureau of WIPO, Swlitzerland.

"Handbook of biological confocal microscopy", Chapter 9, editor J. P. Pawley, Plenum Press, 1995.
International Search Report based on PCT/EP2010/001417 published on May 18, 2005.

\* cited by examiner

MICROSCOPE, IN PARTICULAR LASER SCANNING MICROSCOPE

The present application claims priority from PCT Patent Application No. PCT/EP2010/001417 filed on Mar. 6, 2010, which claims priority from German Patent Application No. DE 10 2009 012 874.3 filed on Mar. 12, 2009, the disclosures of which are incorporated herein by reference in their entirety.

BACKGROUND OF THE INVENTION

1. Field of the Invention

The invention is directed to a microscope for optical detection of light radiation excited in a specimen, having a detection beam path for detecting spectral components of the light radiation in a plurality of detection channels. In the microscope, the light radiation arrives at a variable longpass filter or shortpass filter from which reflected and/or transmitted components are reflected back with a parallel offset, and any transmitted components arrive at a detector after at least one back-reflection of this kind

2. Description of Related Art

Figure 1:
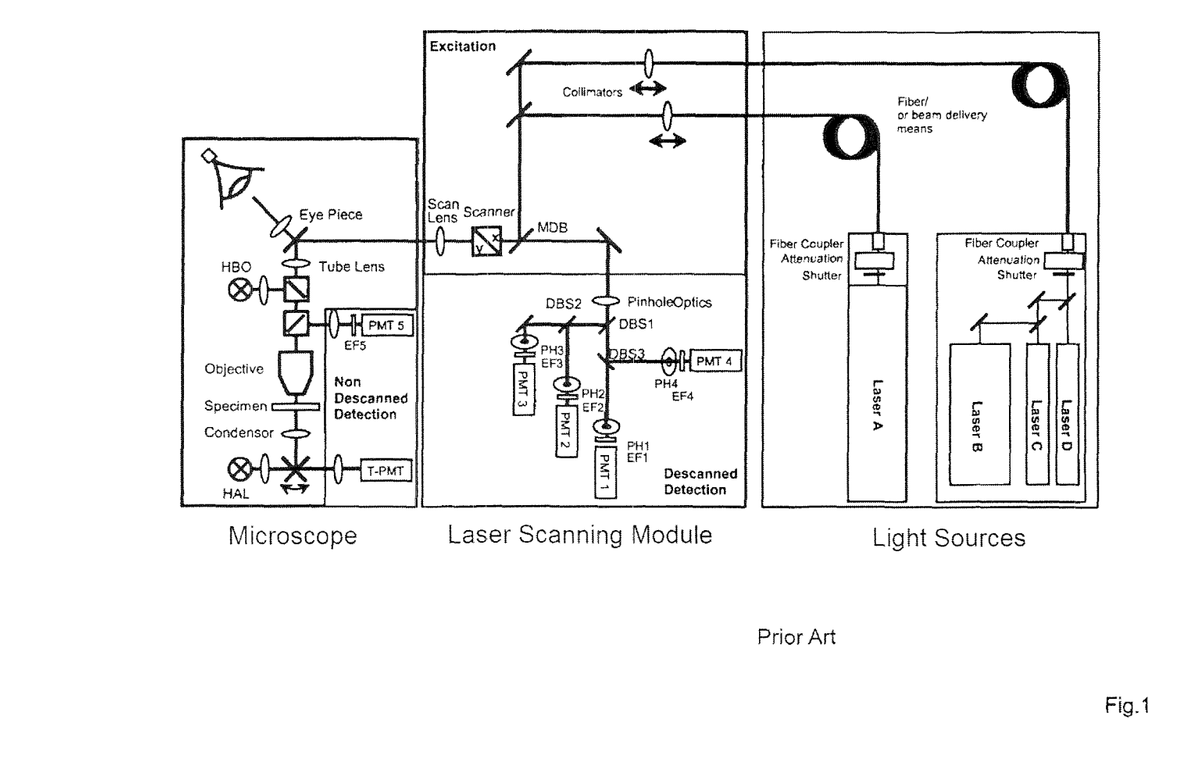
FIG. 1 shows a laser scanning microscope according to the prior art.

In a laser scanning microscope according to the prior art (FIG. 1), light from the light sources (lasers A-D) passes a beamsplitter (MDB), scanners, scanning optics (scanning lens), tube lens, and objective so as to impinge on the specimen in a punctiform manner. Fluorescent light, for example, is excited in the specimen and is collected through the objective and arrives at the beamsplitter again. The beamsplitter is designed in such a way that it transmits the fluorescent light based on the spectral characteristics which are altered relative to the excitation wavelength so that the detection light is focused by pinhole optics through confocal diaphragms (PH 1-4) and subsequently arrives at detectors (PMT 1-4). An emission filter (EF 1-4) is provided in front of each detector in a fluorescence microscope for suppression of the excitation light. Splitting into individual detection channels is carried out by secondary color splitters (DBS1-4). According to the prior art, different emission filters or secondary color splitters which are arranged on a wheel, for example, are swung in for adjusting the spectral characteristics of the detection channels. The illumination spot is scanned over the specimen by means of the scanner. The specimen signals are combined in a computer to form an image.

Further details on prior art can be found in "Handbook of biological confocal microscopy", Chapter 9, editor: J. P. Pawley, Plenum Press, 1995. Various arrangements are known for spectrum-dependent influencing of detection light, all of which have disadvantages.

In DE 19835068A1, only one wavelength or one band can be adjusted by angle-dependent interference filters.

DE19835070A1 describes only a combination of graduated filters, each of which adjusts only one wavelength or one band.

In DE 102004029733A1, two bandpass filters are required. The use of even three detection channels would require four filters and four movements to be controlled and adjusted.

In DE 102006034908, there is a splitting into only two beam paths with limited flexibility if costs are to be kept low.

SUMMARY OF THE INVENTION

It is the object of the invention to make possible a method and an arrangement which allow a flexible spectral beam separation of the detection light with high efficiency into two different detection channels so that the spectral characteristics of the detection channels can be adapted to the spectral characteristics of the fluorescence of the dye. In so doing, no spectral components are lost between adjoining bands. By reducing the mechanical and optical components, the arrangement can realize imaging characteristics less expensively compared to the prior art. These objects are realized by means of the arrangements described in the following.

The invention is directed to an arrangement for flexible adjustment of detection channels for efficient detection in confocal imaging particularly in a laser scanning microscope. The arrangement is described by way of example with reference to multichannel detection.

BRIEF DESCRIPTION OF THE DRAWINGS

FIG. 2a schematically shows of a variable longpass filter;

FIG. 2b shows spectral characteristics of the variable longpass filter of FIG. 2a;

FIG. 2c shows an example of a dependency of the cut-off wavelength of the longpass filter of FIG. 2a on location z;

FIG. 4 shows the spectral regions (represented as boxes) which are detected by the individual detectors (a-d) of the example shown in FIG. 3a.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 2:
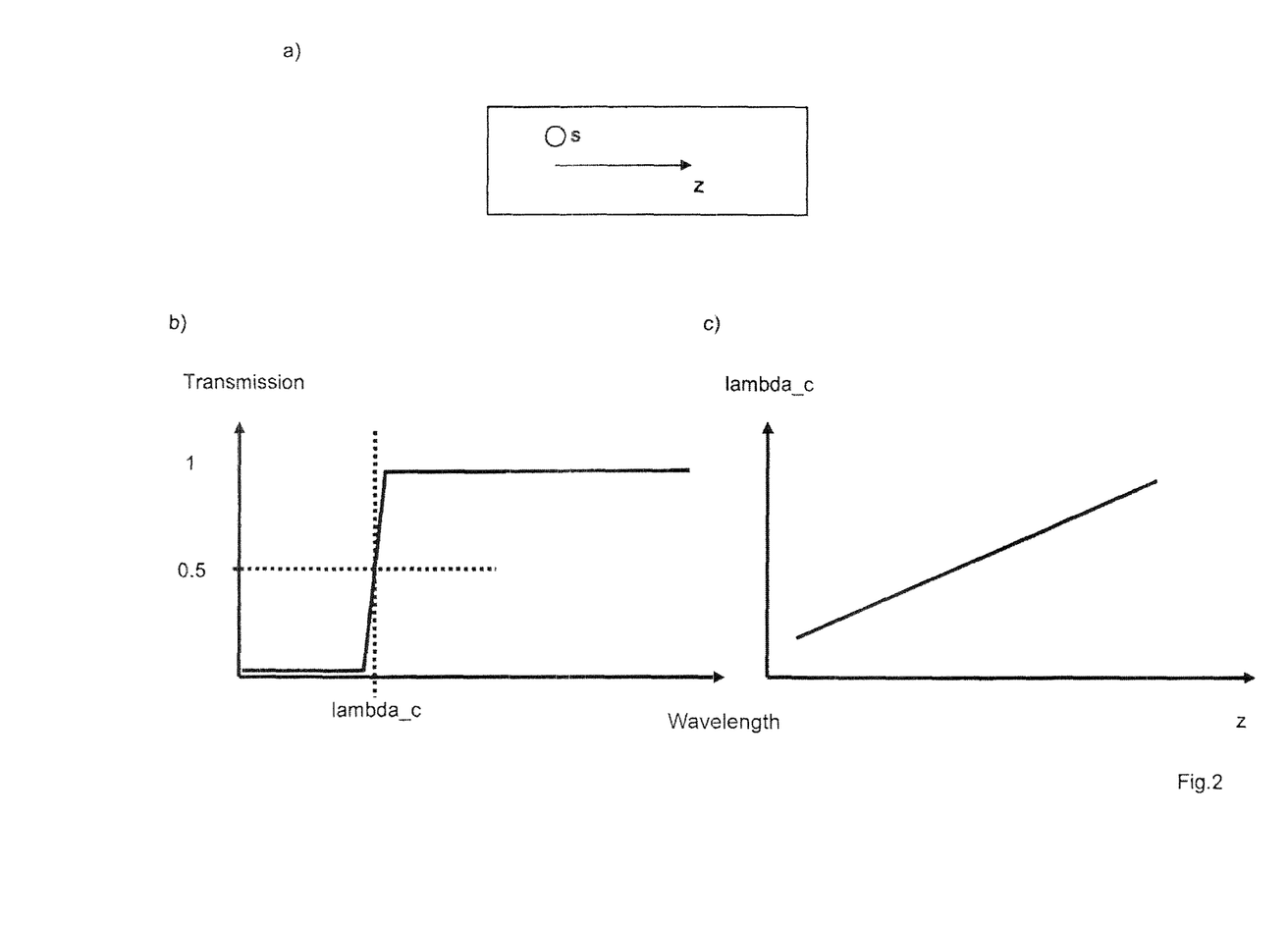

The object according to the invention is realized through the use of a variable longpass filter which is shown schematically in FIG. 2a. With respect to its spectral characteristics, it is characterized in that the cut-off wavelength changes along the z direction. By cut-off wavelength is meant herein the wavelength at which the transmission is exactly 50% of the maximum transmission. In FIG. 2b, this wavelength is designated by lambda_c. FIG. 2c shows, by way of example, a dependency of the cut-off wavelength on location z. In this case, the cut-off wavelength increases linearly.

Figure 3A:
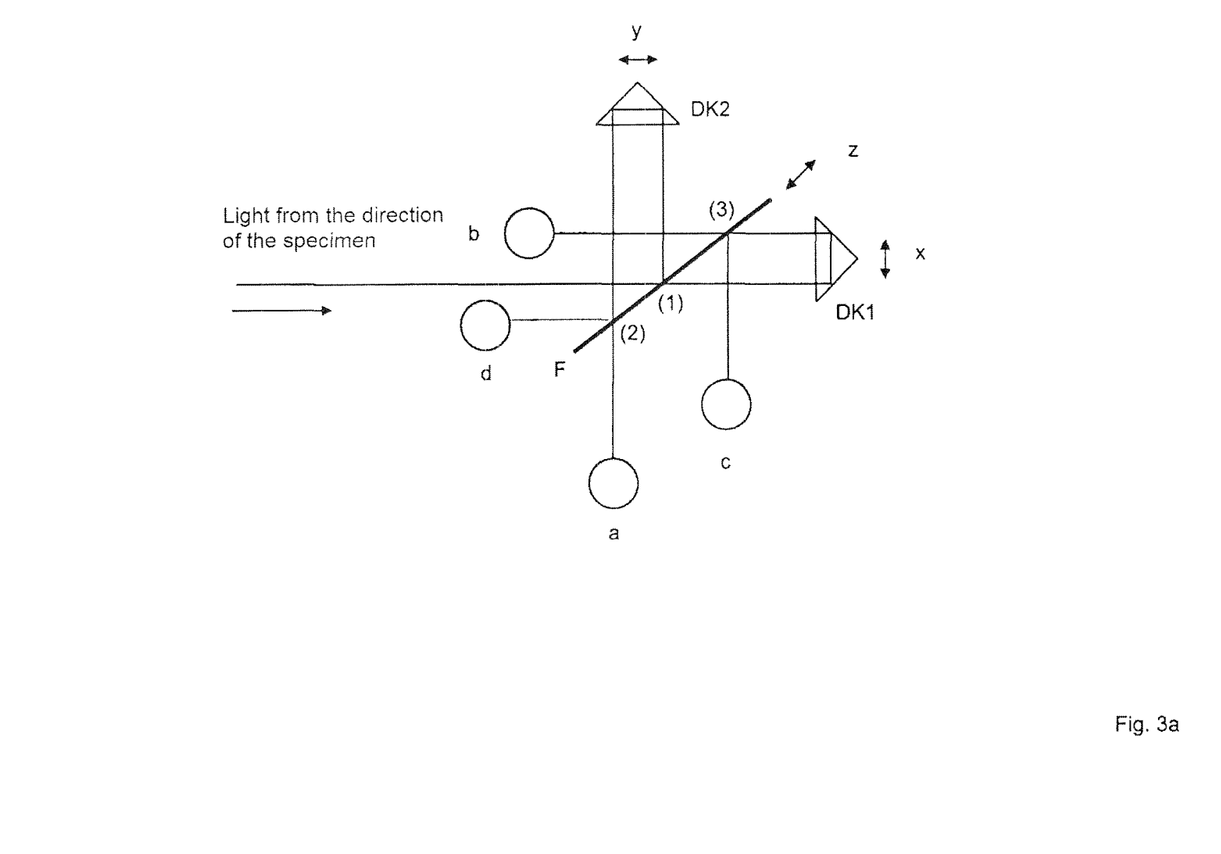
FIG. 3a shows an example of a detection arrangement for flexible separation of the fluorescence radiation into three detection channels.

A detection arrangement for flexible separation of the fluorescence radiation into three detection channels is shown by way of example in FIG. 3a). The light arrives at the variable longpass filter (F) from the direction of the specimen. It is arranged at an angle to the optical axis. Accordingly, reflected or transmitted light components can reach detectors outside the optical axis in a space-saving manner. In the present instance, it has, for example, a continuous increase in the cut-off wavelength from the bottom up. It is constructed as a highpass filter (i.e., light above the cut-off wavelength is transmitted and light below the cut-off wavelength is reflected).

Accordingly, spectral components above the cut-off wavelength (1) pass through F in the direction of a roof prism (DK1). Light below the cut-off wavelength (1) is reflected in the direction of a second roof prism (DK2).

Both roof prisms are arranged so as to be movable along the x and y axes, respectively, in each instance perpendicular to the optical axis. In this way, the wavelength range affected by DK1, DK2 can be adjusted. The detectors can advantageously be displaced so as to be coupled therewith.

Through the roof prisms, the light is offset in a spatially parallel manner and reflected back in itself and again arrives at the longpass filter (F). The light from the direction of DK1 impinges on the longpass filter at the location of the cut-off wavelength (3). Light above the cut-off wavelength (3) and above wavelength (1) is transmitted in the direction of detector (b). The light below the cut-off wavelength (3) and likewise above wavelength (1) is reflected by F in the direction of detector (c). The light which was reflected in direction of DK2 and which lies below the cut-off wavelength 1 impinges on the longpass filter at the location of cut-off wavelength (1) after passing through DK2. Light above cut-off wavelength (2) and below wavelength (1) is transmitted in the direction of detector (a). Light below cut-off wavelength (2) travels (is reflected) in the direction of a detector d.

Figure 3B:
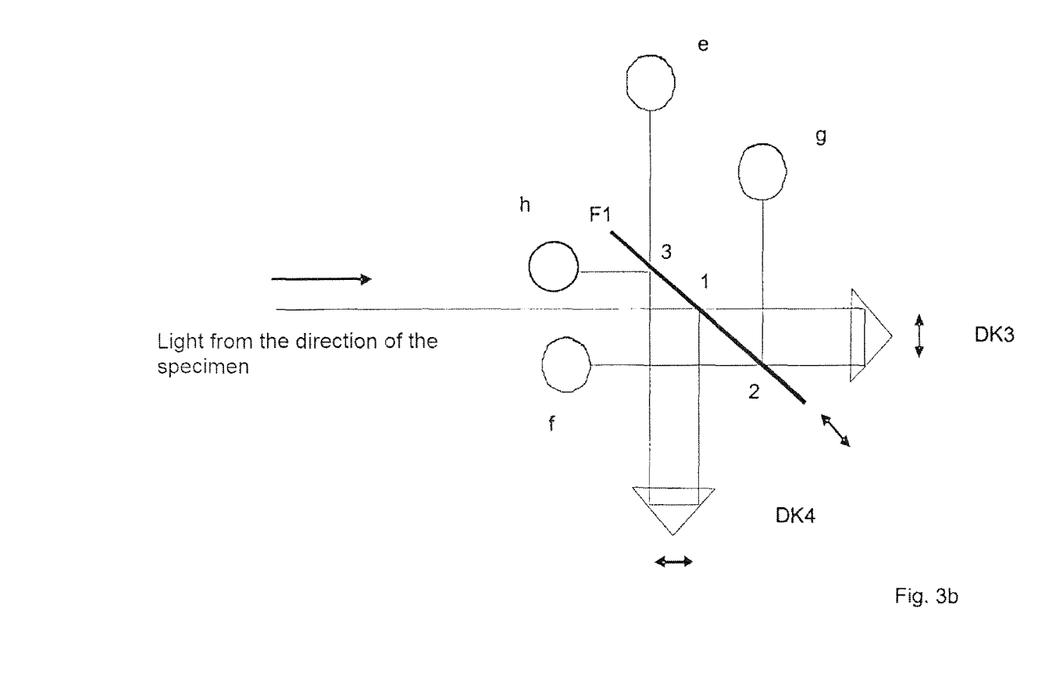
FIG. 3b shows a lowpass filter F1 having a continuous increase in the cut-off wavelength from the bottom up.

FIG. 3b shows a lowpass filter F1 having a continuous increase in the cut-off wavelength from the bottom up, wherein the wavelength above the cut-off wavelength is reflected and wavelengths below the cut-off wavelength are transmitted.

In principle, the arrangement is constructed in a mirror-inverted manner relative to the illustration in FIG. 3a. At the location of cut-off wavelength 1, light of a wavelength below 1 is transmitted in the direction of DK 3 and travels back to F1 at location 2, where wavelength components smaller that (2) are transmitted in the direction of detector f and components greater than (2) and below (1) are reflected in the direction of a detector g.

Components above wavelength (1) are reflected at F1 and arrive via DK4 at location (3) of F1, where components smaller then (3) but greater than (1) are transmitted in the direction of detector e, and components greater than (3) are reflected in the direction of a detector h.

Figure 4:
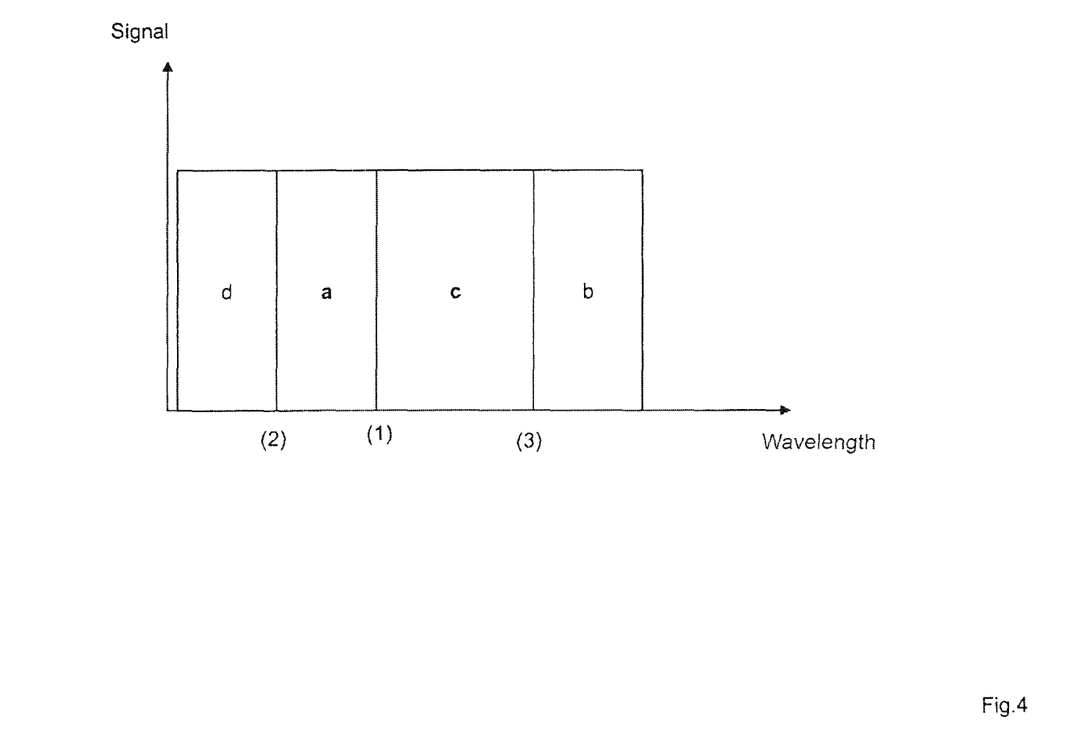

Referring to the example in FIG. 3a, FIG. 4 shows the spectral regions (represented as boxes) which are detected by the individual detectors (a-d). Each of the cut-off wavelengths (1-3) is shown. The position of the cut-off wavelength (1) can be changed by the displacement of the longpass filter (F) along z at an angle to the optical axis. The position of cut-off wavelengths (3) and (2), respectively, is influenced by displacing DK1 and DK2, respectively. In this way, any widths and positions of bands (a-c) can be realized. It is particularly advantageous that in so doing the bands (d), (a), (c) and (b) adjoin each other directly without spectral gaps. Accordingly, no spectral fluorescence components are lost during the spectral splitting into detection channels.

Figure 5:
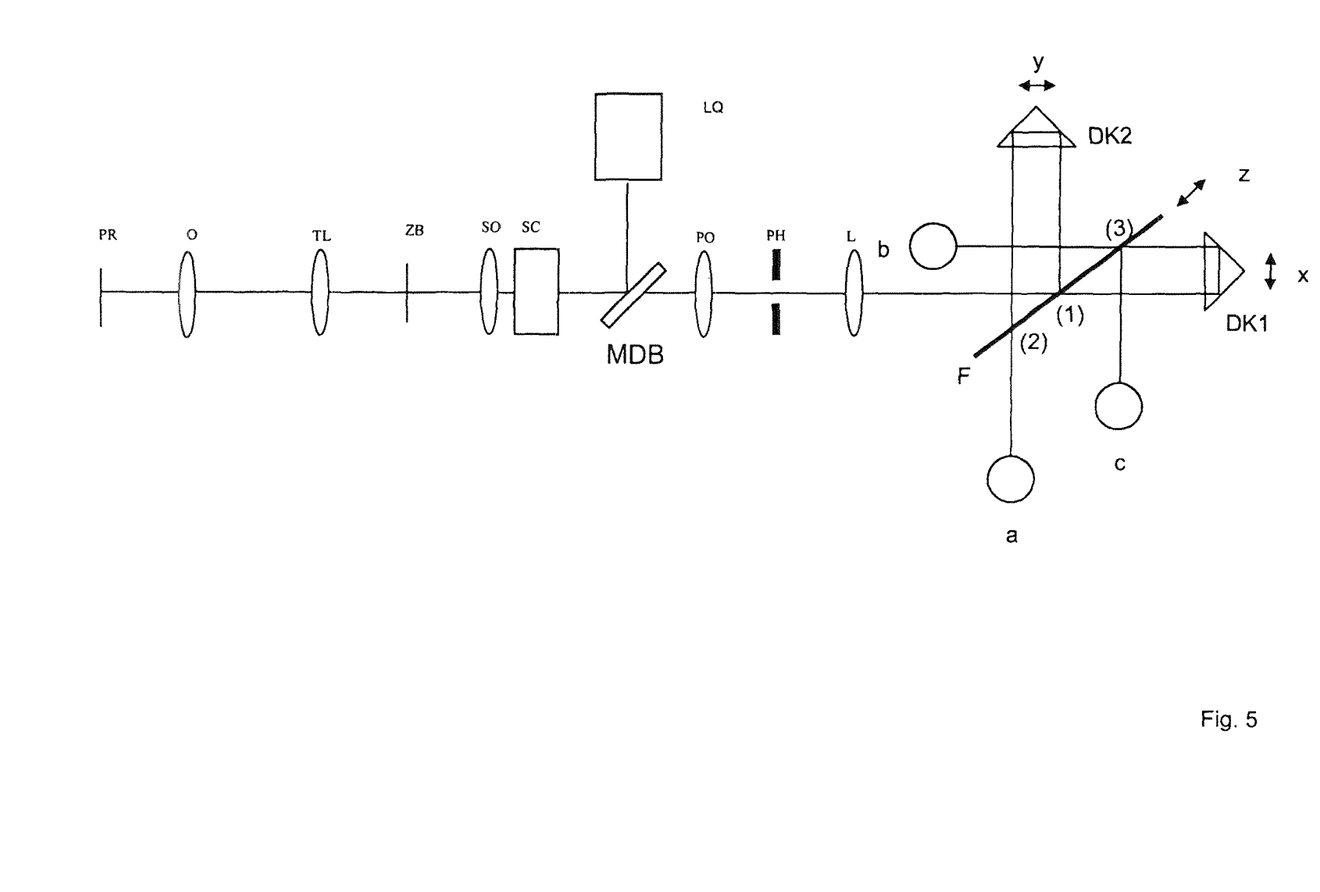
FIG. 5 shows an embodiment of a detection arrangement in a laser scanning microscope.

FIG. 5 shows the detection arrangement in a laser scanning microscope. The detection light (e.g., fluorescence) is excited in the specimen in a manner analogous to the prior art arrangement described in FIG. 1. Specimen light collected through the objective (O) passes via the tube lens (TL), scanning optics (SO), and scanner (SC) in the direction of the main color splitter (MDB). The latter preferably transmits the specimen light in the direction of the pinhole optics (PO). The light is focused through PO in a confocal pinhole (PH). Additional optics (L) collimate the light after the pinhole. It then arrives in the detection arrangement described with reference to FIG. 3.

The arrangement according to the invention was described by way of example with reference to four detection channels and with the use of a variable longpass filter. The quantity of detection channels can be increased by corresponding back-reflection with additional roof prisms of a detection channel. In addition, a shortpass filter (FIG. 3b) can also be used instead of the longpass filter after adjustment of the DK (rotation by 180°).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A microscope for optical detection of light radiation excited in a specimen, comprising:
    a detection beam path for detecting spectral wavelength components of the light radiation in a plurality of detection channels;
    a longpass filter or shortpass filter arranged in the detection beam path, said longpass filter or shortpass filter being changeable with respect to the wavelength components it reflects and transmits;
    at least one reflector configured to generate a parallel offset of either a reflected radiation a back-reflection or both in the direction of the longpass filter or shortpass filter for the reflected or transmitted wavelength component; and
    wherein detectors are configured to receive the wavelength components reflected or transmitted by the longpass filter or shortpass filter after at least one back-reflection and a further reflection or transmission through said longpass or shortpass filter.

2. The microscope according to claim 1;
    wherein the longpass filter or shortpass filter is a variable edge filter which has different splitting into transmitted wavelength components and reflected wavelength components along its longitudinal extension.

3. The microscope according to claim 1;
    wherein the longpass filter or shortpass filter has a variable cut-off wavelength along its profile which determines a ratio of wavelength components which are reflected to the wavelength components which are transmitted.

4. The microscope according to claim 3;
    wherein the longpass filter or shortpass filter is displaceable along the direction of the variable cut-off wavelength.

5. The microscope according to claim 1;
    wherein at least one reflector is displaceable perpendicular to the incident direction of the light.

6. The microscope according to claim 5;
    wherein a displaceable detector is displaced to as to be coupled with the reflector.

7. The microscope according to claim 1;
    wherein the reflector is a roof prism or roof mirror.

8. The microscope according to claim 1;
    wherein the longpass filter or shortpass filter is a variable edge filter which has different splitting into transmitted wavelength components and reflected wavelength components along its longitudinal extension.

9. The microscope according to claim 1;
wherein the longpass filter or shortpass filter has a variable cut-off wavelength along its profile which determines a ratio of wavelength components which are reflected to the wavelength components which are transmitted.

10. The microscope according to claim 9;
wherein longpass filter or shortpass the filter is displaceable along the direction of the variable cut-off wavelength.

11. The microscope according to claim 1;
wherein at least one reflector is displaceable perpendicular to the incident direction of the light.

12. The microscope according to claim 11
wherein a displaceable detector is displaced so as to be coupled with the reflector.

13. The microscope according to claim 1;
wherein the reflector is a roof prism or roof mirror.

* * * * *